US012611165B2

(12) United States Patent
Franz et al.

(10) Patent No.: US 12,611,165 B2
(45) Date of Patent: Apr. 28, 2026

(54) FETAL ULTRASOUND IMAGE PROCESSING

(71) Applicant: KONINKLIJKE PHILIPS N.V., Eindhoven (NL)

(72) Inventors: Astrid Ruth Franz, Hamburg (DE); Cristian Lorenz, Hamburg (DE); Eliza Teodora Orasanu, Hamburg (DE); Alexander Schmidt-Richberg, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/708,796

(22) PCT Filed: Oct. 27, 2022

(86) PCT No.: PCT/EP2022/080031
§ 371 (c)(1),
(2) Date: May 9, 2024

(87) PCT Pub. No.: WO2023/094102
PCT Pub. Date: Jun. 1, 2023

(65) Prior Publication Data
US 2025/0017556 A1 Jan. 16, 2025

(30) Foreign Application Priority Data
Nov. 23, 2021 (EP) .................................... 21210014

(51) Int. Cl.
*A61B 8/08* (2006.01)
*A61B 8/00* (2006.01)
(52) U.S. Cl.
CPC .......... *A61B 8/0866* (2013.01); *A61B 8/0875* (2013.01); *A61B 8/461* (2013.01); *A61B 8/483* (2013.01); *A61B 8/54* (2013.01)

(58) Field of Classification Search
CPC .................................................... A61B 8/0866
See application file for complete search history.

(56) References Cited

U.S. PATENT DOCUMENTS

| | | | |
|---|---|---|---|
| 5,997,479 A | 12/1999 | Savord et al. | |
| 6,013,032 A | 1/2000 | Savord | |

(Continued)

FOREIGN PATENT DOCUMENTS

| | | |
|---|---|---|
| WO | 2020133236 A1 | 7/2020 |

OTHER PUBLICATIONS

T. Vrtovec et al., "Automated curved planar reformation of 3D spine images", Physics in Medicine and Biology, vol. 50, pp. 4527-4540, Feb. 2005 (Year: 2005).*

(Continued)

*Primary Examiner* — Nyrobi Celestine

(57) ABSTRACT

A fetal imaging method involves detecting (102) a spine centerline in a 3D ultrasound image, and determining (104) a first plane which is a sagittal plane of best fit through the spine centerline. A second, coronal plane, is also determined (108), and the image of the spine is projected onto the second plane, and the second plane and the projection of the spine image onto the second plane are displayed (110). In accordance with the invention, a measure of fit error of the spine centerline to the first plane is derived. If the measure of fit error is below a threshold, the first plane and the image of the spine is displayed (106). If the measure of fit error is not below the threshold, the image of the spine image is projected onto the first plane, and the first plane and the projected image of the spine is displayed (106).

20 Claims, 5 Drawing Sheets

(56)                    References Cited

U.S. PATENT DOCUMENTS

| | | |
|---|---|---|
| 6,283,919 B1 | 9/2001 | Roundhill et al. |
| 6,443,896 B1 | 9/2002 | Detmer |
| 6,458,083 B1 | 10/2002 | Jago et al. |
| 6,530,885 B1 | 3/2003 | Entrekin et al. |
| 6,623,432 B2 | 9/2003 | Powers et al. |
| 2002/0136437 A1 | 9/2002 | Gerard et al. |
| 2003/0194057 A1* | 10/2003 | Dewaele ................... G06T 7/60 |
| | | 378/210 |
| 2008/0287796 A1 | 11/2008 | Kiraly et al. |
| 2013/0079680 A1* | 3/2013 | Stein ..................... A61F 2/4611 |
| | | 606/90 |
| 2019/0192099 A1 | 6/2019 | Jia et al. |
| 2020/0234435 A1 | 7/2020 | Raynaud et al. |
| 2021/0085283 A1* | 3/2021 | Zheng ................. G01S 15/8993 |

OTHER PUBLICATIONS

International Search Report and Written Opinion for PCT/EP2022/080031, Mailing date: Feb. 22, 2023, 9 pages.

Leung, K.Y., et al., "Three-dimensional extended imaging: a new display modality for three-dimensional ultrasound examination," Ultrasound Obstet Gynecol., 2005, vol. 26, Issue 3, pp. 244-251.

Papageorghiou, A. et al., "International standards for fetal growth based on serial ultrasound measurements: the Fetal Growth Longitudinal Study of the INTERGROWTH—21st Project," Lancet, 2014, vol. 384, Issue 9946, pp. 869-879.

Franz, A. et al., "Deep Learning Based Spine Centerline Extraction in Fetal Ultrasound," Bildverarbeitung für die Medizin, 2021, pp. 263-268.

* cited by examiner

FETAL ULTRASOUND IMAGE PROCESSING

CROSS-REFERENCE TO PRIOR APPLICATIONS

This application is the U.S. National Phase application under 35 U.S.C. § 371 of International Application No. PCT/EP2022/080031, filed on Oct. 27, 2022, which claims the benefit of European Patent Application No. 21210014.3, filed on Nov. 23, 2021. These applications are hereby incorporated by reference herein.

FIELD OF THE INVENTION

This invention relates to the processing of fetal ultrasound images.

BACKGROUND OF THE INVENTION

Ultrasound is the modality of choice for fetal screening as it is able to show fetal anatomy in sufficient detail, while at the same being cost effective with no known adverse effects. Fetal screening allows for detecting abnormalities at an early gestational age, such that therapeutically suitable interventions can be planned and performed as required. Currently, there is a trend towards using 3D ultrasound, since a 3D image contains much more spatial information about the location of several organs with respect to each other and it allows for a variety of workflow optimizations.

A major part of the fetal examination is performed at 18 to 22 weeks gestational age with specific recommended standard measurements, for example as outlined in A. T. Papageorghiou, et al.: International standards for fetal growth based on serial ultrasound measurements: The Fetal Growth Longitudinal Study of the INTERGROWTH-21st Project, The Lancet 384, 869-879, 2014.

These measurements are related to the size of certain bones and structures and provide an insight into the fetal growth. Furthermore, structures are qualitatively investigated to detect anomalies.

One of these structures is the fetal spine. Standard views are required, for instance the ossification centers are best visible in sagittal views, abnormal curvature can be detected in sagittal and coronal views, and in axial (transverse) planes each vertebra can be investigated.

WO 2020/133236 for example discloses a method for detecting deformation of a spine.

Searching for optimal view planes for investigating the fetal spine is a demanding and time-consuming task. It requires an optimal manual positioning of the ultrasound probe and needs to be repeated in case the fetus is moving. Furthermore, due to the curvature of the spine, it is not always possible to find a plane which contains the whole spine. In such a case, a sweep through a range of neighboring view planes is required to cover the whole spine. Such an investigation requires several minutes to be performed completely.

There is a need for an improved way to obtain standard fetal ultrasound images.

SUMMARY OF THE INVENTION

The invention is defined by the independent claims. Dependent claims define advantageous embodiments.

According to examples in accordance with an aspect of the invention, there is provided a computer-implemented fetal imaging method comprising:

obtaining a 3D ultrasound image;

detecting a spine centerline in the 3D ultrasound image;

determining a first plane which is a sagittal plane of best fit through the spine centerline; displaying the first plane and the image of the spine or a projection of the image of the spine onto the first plane;

determining a second plane, perpendicular to the first plane, which is a coronal plane of best fit to the spine centerline; and displaying the second plane and a projection of the image of the spine onto the second plane.

This method displays the shape of the spine in the sagittal and coronal planes, by detecting the spine centerline so that projections of the spine image may be performed using the centerline as a representation of the spine location. If there is significant curvature out of the sagittal plane, a projection of the spine image may be provided onto the sagittal plane. The spine image is projected onto the coronal plane since the spine does not lie within a coronal plane.

The method thus provides an automatic generation of view planes of interest. The spine centerline is obtained using an image processing algorithm and from this sagittal and coronal views are obtained which each contain a whole view of the spine, from the two orthogonal directions. Thus, a three dimensional spine shape can quickly be assessed from automatically generated views.

The first plane is for example the mid-sagittal plane.

The method further comprises:

deriving a measure of fit error of the spine centerline to the first plane;

if the measure of fit error is below a threshold, displaying the first plane and the image of the spine;

if the measure of fit error is not below the threshold, projecting the image of the spine onto the first plane, and displaying the first plane and the projected image of the spine.

In this way, if the spine is not contained in a single sagittal plane, a projection of the spine image is made onto the sagittal plane, using the spine centerline to define the projection transformation, thereby to project the image of the spine onto the first plane. In this way, a view is ensured containing the whole spine. Presenting such automatically generated standard views to the physician can significantly speed up the investigation time. A manual view plane selection typically requires several minutes, whereas the automated approach enables views to be generated in less than one minute.

The method avoids the needs for manually positioning the ultrasound probe.

If the measure of fit error is above a second threshold, an output may be provided indicating high spine curvature (out of the sagittal plane). This provides automated detection of spine curvature problems.

The method may comprise deriving a measure of fit error of the spine centerline to the second plane, wherein if the measure of fit error is above a third threshold, providing an output indicating high spine curvature. This provides automated detection of spine curvature problems out of the coronal plane.

The method may further comprise deriving a sequence of planes perpendicular to the spine centerline. Thus, a sweep of axial views can also be computed automatically.

The method for example comprises implementing a user interface allowing a user to sweep though the sequence in order to view each vertebra in an axial view. Thus, a user can sweep through standard axial views.

The method may further comprise defining a volume of interest around the spine and performing volume rendering.

The invention also provides a controller for controlling the processing of a 3D fetal ultrasound image, wherein the controller is adapted to implement the method as defined above.

The invention also provides an ultrasound system, the system comprising:

an ultrasonic probe, the ultrasonic probe comprising an array of transducer elements, wherein the ultrasonic probe is adapted to obtain a 3D fetal ultrasound image;

a controller as defined above; and a display device for displaying the first and second planes and the spine within these planes and/or projected onto these planes.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
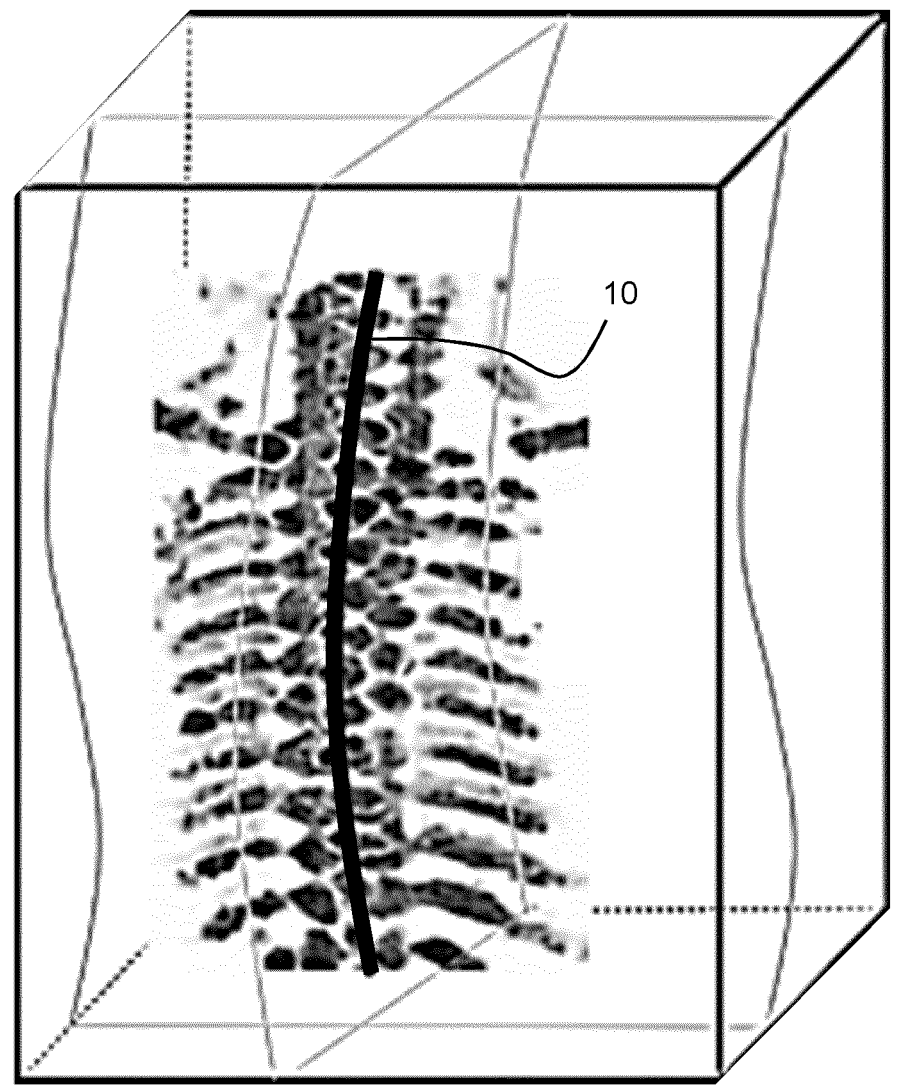
FIG. 1 shows an illustration of the 3D volume data obtained by a 3D ultrasound scan.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a fetal imaging method which involves detecting a spine centerline in a 3D ultrasound image, and determining a first plane which is a sagittal plane of best fit through the spine centerline. The first plane and the image of the spine in the first plane and/or a projection of the image of the spine onto the first plane are displayed. A second, coronal plane, is also determined, and the image of the spine is projected onto the second plane, and the second plane and the projection of the spine onto the second plane are displayed.

FIG. 1 shows an illustration of the 3D volume data obtained by a 3D ultrasound scan. From the 3D scan, the spin centerline 10 is detected.

An example of an algorithm for detecting the spine centerline is applied for example as described in A. Franz, et al.: Deep learning based spine centerline extraction in fetal ultrasound. In: C. Palm et al. (eds.): Bildverarbeitung für die Medizin, 263-268, 2021. The result is a sequence of points located in the spinal canal.

A first plane is then defined, which is a sagittal plane of best fit through the spine centerline. In particular, the mid-sagittal plane S is defined as that plane where the quadratic sum q of the distances of spine centerline points to the plane is minimal.

Figure 2:
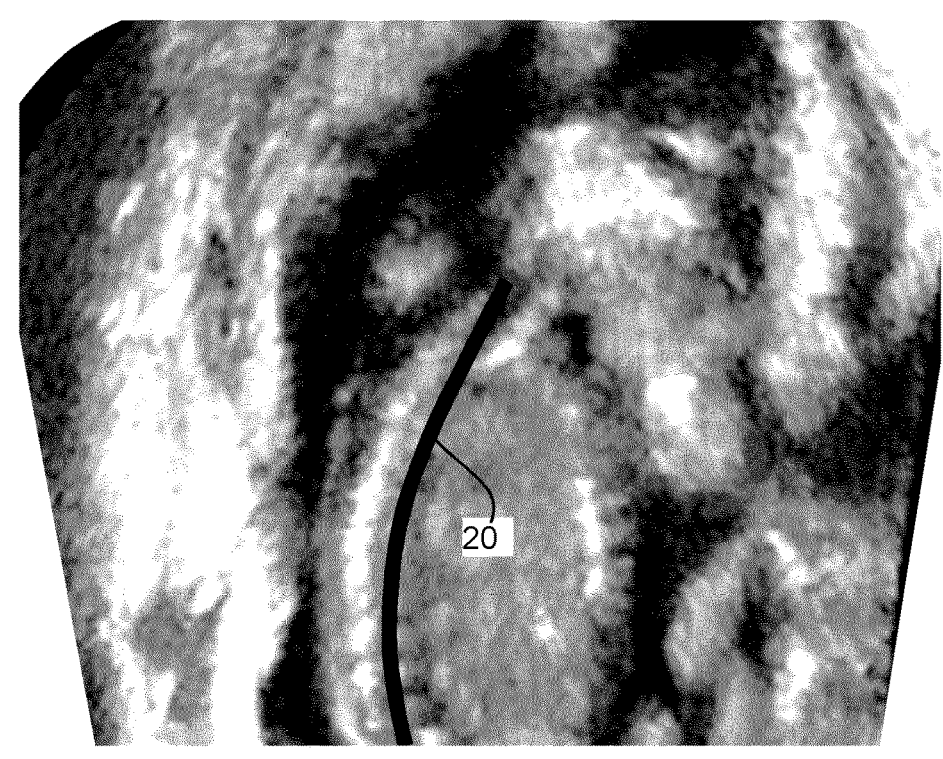
FIG. 2 shows a sagittal plane with a spine image projected onto the plane.

FIG. 2 shows this sagittal plane.

This sum q serves as a measure of fit error of the spine centerline to the first plane. If the measure of fit error q is below a threshold, the first plane and the spine image are displayed as shown in FIG. 2. In particular, if q is below a pre-defined threshold, it means the spine centerline points are nearly contained in the plane S. Hence the plane S can be displayed together with the image along the spine centerline.

If the measure q of fit error is not below the threshold, the spine image is projected onto the first plane, and the plane is then displayed with the projected spine image. The image will again be as shown in FIG. 2. Thus, if q exceeds the threshold, then the image along the spine centerline needs to be projected onto the plane S, yielding the projected view of the 3D data set.

FIG. 2 shows the spine centerline 20 or projected spine centerline 20 for illustrative purposes. In practice, the practitioner wishes to view the actual spine image, and the centerline does not need to be displayed. The spine centerline, as obtained from the analysis of the 3D ultrasound volume, is used to create the transformation of the 3D volume data so that the spine image is projected onto the first plane. Thus, the spine centerline is used for the purposes of defining the mid-sagittal plane and creating the mapping to enable the spine image data in the 3D data volume to be projected onto a 2D plane.

If the measure q of fit error exceeds a further clinically relevant threshold, it could indicate an abnormally high spine curvature, corresponding for instance to scoliosis. The visualizations can then be flagged accordingly, potentially indicating regions of high deviation.

A second plane is also determined, perpendicular to the first plane, which is a coronal plane of best fit to the spine centerline. The coronal plane C is thus defined as being perpendicular to S and as having the minimal quadratic sum of distances to the spine centerline points. This plane normally does not contain all spine centerline points, hence spine image is projected onto the plane C, yielding a projected view of the 3D data set.

Figure 3:
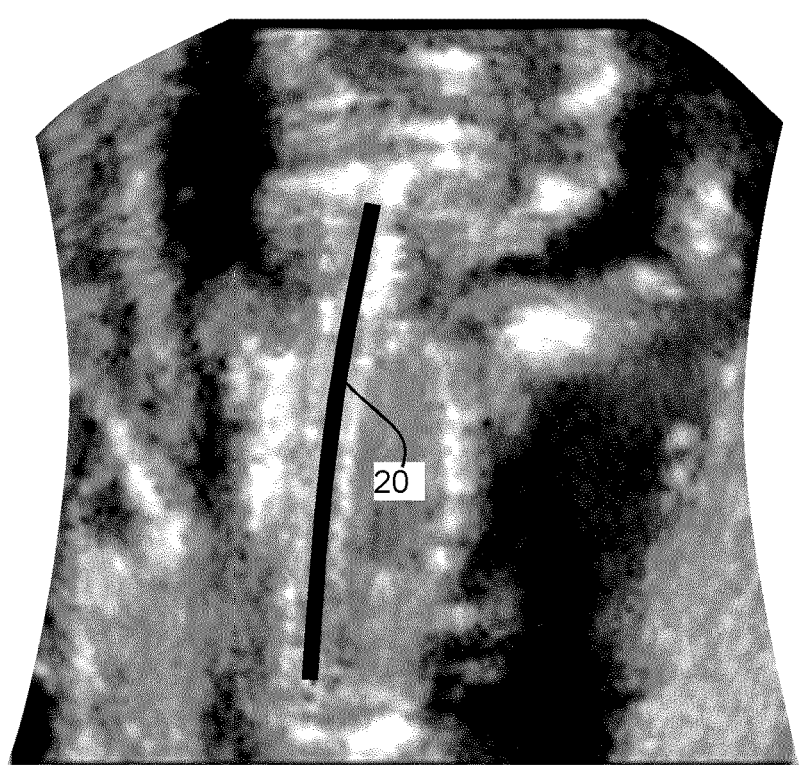
FIG. 3 shows a coronal plane with a spine image projected onto the plane.

FIG. 3 shows this second, coronal, plane. The spine is projected onto the second plane, and the second plane and the projected spine image are displayed. Again, the projected spine centerline 20 is shown for illustration purposes and in clinical practice it would not be shown since it could distract the physician and may hide important details.

The quadratic sum may also be considered as a measure of fit error of the spine centerline to the second plane. This may also be used as a measure of spine curvature out of the coronal plane. Thus spine curvatures in the two orthogonal directions may be assessed automatically based on the fitting of the spine centerline to the two planes.

If required, a sequence of planes perpendicular to the spine centerline may be computed. The investigating physician can sweep through these planes in order to investigate each vertebra in an axial view.

Figure 4:
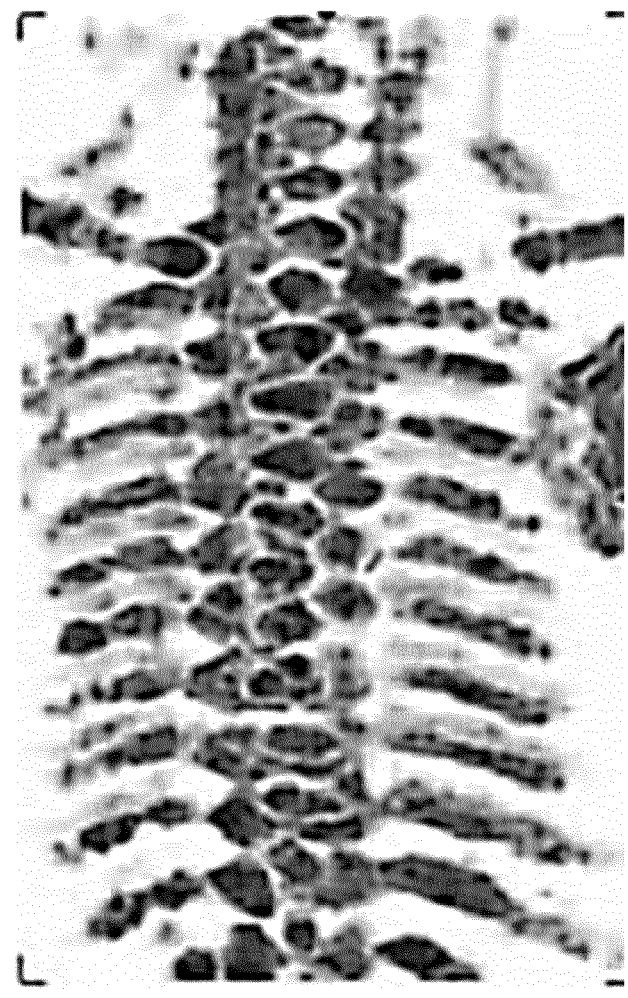
FIG. 4 shows a slab like volume of interest defined around the spine.

Similarly, if required, a slab like volume of interest can be defined around the spine, to allow a direct volume rendering of the spine anatomy. Such a volume of interest is shown in FIG. 4.

Figure 5:
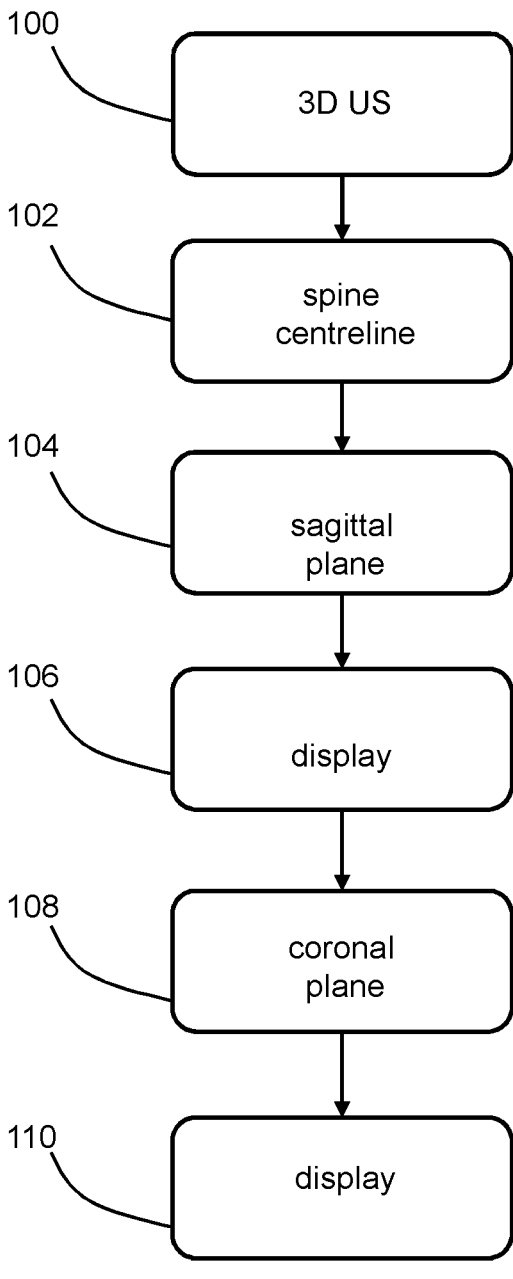
FIG. 5 shows a computer-implemented fetal imaging method.

FIG. 5 shows a computer-implemented fetal imaging method.

In step 100, a 3D ultrasound image is obtained.

In step 102, a spine centerline is detected in the 3D ultrasound image.

In step 104, a first plane which is a sagittal plane of best fit through the spine centerline is determined.

In step 106, the first plane is displayed with the image of the spine or a projection of the image of the spine onto the first plane. In particular, in accordance with the invention, a measure of fit error of the spine centerline to the first plane is derived. If the measure of fit error is below a threshold, the first plane and the image of the spine is displayed. If the measure of fit error is not below the threshold, the image of the spine image is projected onto the first plane, and the first plane and the projected image of the spine is displayed.

In step 108, a second plane, perpendicular to the first plane, which is a coronal plane of best fit to the spine centerline is determined.

In step 110, the second plane is displayed with a projection of the image of the spine onto the second plane.

Of course, the steps of the method may be performed in a different order. For example, both planes can be derived (in either order) before any display of information.

Figure 6:
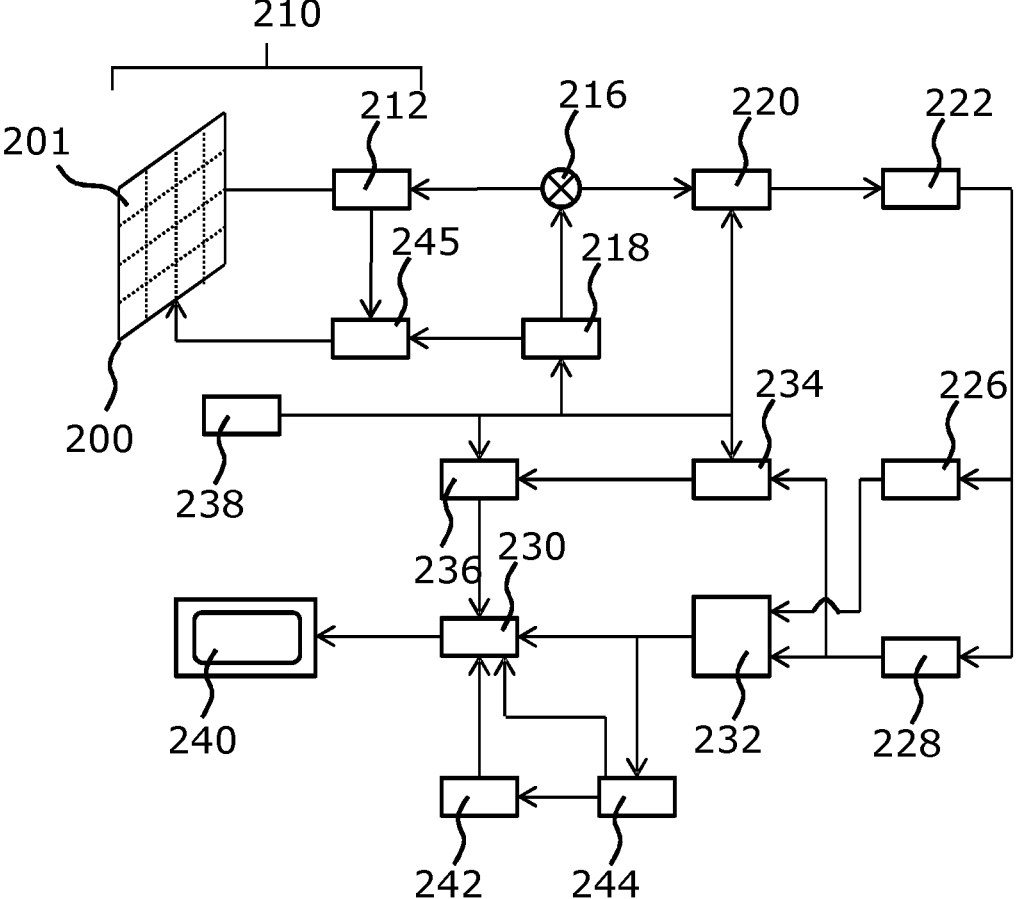
FIG. 6 shows an exemplary ultrasound diagnostic imaging system which can perform the image processing of the invention.

For completeness, the general operation of an exemplary ultrasound diagnostic imaging system will first be described, with reference to FIG. 6, and with emphasis on the signal processing function of the system since this invention relates to the processing of the signals measured by the transducer array.

The system comprises an array transducer probe 210 which has a CMUT transducer array 200 for transmitting ultrasound waves and receiving echo information. The transducer array 200 may alternatively comprise piezoelectric transducers formed of materials such as PZT or PVDF. The transducer array 200 is a two-dimensional array of transducers 201 capable of scanning in three dimensions for 3D imaging.

The transducer array 200 is coupled to a microbeamformer 212 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 212 is coupled by the probe cable to a transmit/receive (T/R) switch 216 which switches between transmission and reception and protects the main beamformer 220 from high energy transmit signals when a microbeamformer is not used and the transducer array is operated directly by the main system beamformer. The transmission of ultrasound beams from the transducer array 210 is directed by a transducer controller 218 coupled to the microbeamformer by the T/R switch 216 and a main transmission beamformer (not shown), which receives input from the user's operation of the user interface or control panel 238.

One of the functions controlled by the transducer controller 218 is the direction in which beams are steered and focused. Beams may be steered straight ahead from (orthogonal to) the transducer array, or at different angles for a wider field of view. The transducer controller 218 can be coupled to control a DC bias control 245 for the CMUT array. The DC bias control 245 sets DC bias voltage(s) that are applied to the CMUT cells.

In the reception channel, partially beamformed signals are produced by the microbeamformer 212 and are coupled to a main receive beamformer 220 where the partially beamformed signals from individual patches of transducers are combined into a fully beamformed signal. For example, the main beamformer 220 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 222. The signal processor 222 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 12 only the receiver beamformers 212, 220 are shown, for simplicity. In the complete system, there will also be a transmission chain with a transmission micro beamformer, and a main transmission beamformer.

The function of the micro beamformer 212 is to provide an initial combination of signals in order to decrease the number of analog signal paths. This is typically performed in the analog domain.

The final beamforming is done in the main beamformer 220 and is typically after digitization.

The transmission and reception channels use the same transducer array 210 which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 226 and a Doppler processor 228. The B mode processor 226 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 228 processes temporally distinct signals from tissue movement and blood flow for the detection of the motion of substances such as the flow of blood cells in the image field. The Doppler processor 228 typically includes a wall filter with parameters which may be set to pass and/or reject echoes returned from selected types of materials in the body.

The structural and motion signals produced by the B mode and Doppler processors are coupled to a scan converter 232 and a multi-planar reformatter 244. The scan converter 232 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 242 converts the echo signals of a 3D data set into a projected 3D image as viewed from a given reference point as described in U.S. Pat. No. 6,530,885 (Entrekin et al.).

The 2D or 3D images are coupled from the scan converter 232, multi-planar reformatter 244, and volume renderer 242 to an image processor or controller 230 for further enhancement, buffering and temporary storage for display on an image display 240. In addition to being used for imaging, the blood flow values produced by the Doppler processor 28 and tissue structure information produced by the B mode processor 226 are coupled to a quantification processor 234. The quantification processor produces measures of different flow conditions such as the volume rate of blood flow as well as structural measurements such as the sizes of organs and gestational age. The quantification processor may receive input from the user control panel 238, such as the point in the anatomy of an image where a measurement is to be made. Output data from the quantification processor is coupled to a graphics processor 236 for the reproduction of measurement graphics and values with the image on the display 240, and for audio output from the display device 240. The graphics processor 236 can also generate graphic overlays for display with the ultrasound images. These graphic overlays can contain standard identifying information such as patient name, date and time of the image, imaging parameters, and the like. For these purposes the graphics processor receives input from the user interface 238, such as patient name. The user interface is also coupled to the transmit controller 218 to control the generation of ultrasound signals from the transducer array 210 and hence the images produced by the transducer array and the ultrasound system. The transmit control function of the controller 218 is only one of the functions performed. The controller 218 also takes account of the mode of operation (given by the user) and the corresponding required transmitter configuration and band-pass configuration in the receiver analog to digital converter. The controller 218 can be a state machine with fixed states.

The user interface is also coupled to the multi-planar reformatter 244 for selection and control of the planes of multiple multi-planar reformatted (MPR) images which may be used to perform quantified measures in the image field of the MPR images.

The image processing functions described above may for example be performed by the image processor 230.

In accordance with a further aspect of the invention, a computer program product comprises instructions (software) for the image processor or controller 230 to implement the method of the invention. The computer program product may be software that can be downloaded from a server. Alternatively, the computer program product may be a data carrier (e.g. a CD or DVD) comprising the software.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. Measures recited in mutually different dependent claims may be advantageously combined. If the term "adapted to" is used in the claims or description, it is noted the term "adapted to" is intended to be equivalent to the term "configured to". Any reference signs in the claims should not be construed as limiting the scope.

The invention claimed is:

1. A computer-implemented imaging method, the method comprising:

obtaining a 3D ultrasound image, comprising an image of a spine;

detecting a spine centerline in the 3D ultrasound image;

determining a first plane which is a sagittal plane of best fit through the spine centerline;

determining a second plane, perpendicular to the first plane, which is a coronal plane of best fit to the spine centerline;

projecting the image of the spine onto the second plane to generate a projection of the image of the spine onto the second plane;

displaying the determined second plane, and displaying the generated projection of the image of the spine onto the second plane; and deriving a measure of fit error of the determined spine centerline to the first plane;

wherein if the measure of fit error is below a threshold, displaying the first plane and the image of the spine;

wherein if the measure of fit error is not below the threshold, projecting the image of the spine onto the first plane to generate a projection of the image of the spine onto the first plane, and displaying the first plane and the generated projected image of the spine onto the first plane.

2. The method of claim 1, wherein the first plane is the mid-sagittal plane.

3. The method of claim 1, wherein if the measure of fit error is above a second threshold, providing an output indicating high spine curvature.

4. The method of claim 1, comprising deriving a measure of fit error of the spine centerline to the second plane, wherein if the measure of fit error is above a third threshold, providing an output indicating high spine curvature.

5. The method of claim 1, comprising deriving a sequence of planes perpendicular to the spine centerline.

6. The method of claim 1, further comprising allowing a user to sweep though the sequence in order to view each vertebra in an axial view via a user interface.

7. The method of claim 1, further comprising defining a volume of interest around the spine and performing volume rendering.

8. An ultrasound system comprising a controller for controlling processing of a 3D ultrasound image, wherein the controller is adapted to implement a method comprising:

obtaining a 3D ultrasound image, comprising an image of a spine;

detecting a spine centerline in the 3D ultrasound image;

determining a first plane which is a sagittal plane of best fit through the spine centerline;

determining a second plane, perpendicular to the first plane, which is a coronal plane of best fit to the spine centerline;

projecting the image of the spine onto the second plane to generate a projection of the image of the spine onto the second plane;

displaying the determined second plane, and displaying the generated projection of the image of the spine onto the second plane; and deriving a measure of fit error of the determined spine centerline to the first plane;

wherein if the measure of fit error is below a threshold, displaying the first plane and the image of the spine, and wherein if the measure of fit error is not below the threshold, projecting the image of the spine onto the first plane to generate a projection of the image of the spine onto the first plane, and displaying the first plane and the generated projected image of the spine onto the first plane.

9. The ultrasound system of claim 8, further comprising:

an ultrasonic probe, the ultrasonic probe comprising an array of transducer elements, wherein the ultrasonic probe is adapted to obtain a 3D ultrasound image; and a display device for displaying the first and second planes and the spine within these planes and/or projected onto these planes.

10. A non-transitory storage medium comprising a computer program product, the computer program product comprising instructions for a controller to implement a method comprising:

obtaining a 3D ultrasound image, comprising an image of a spine;

detecting a spine centerline in the 3D ultrasound image;

determining a first plane which is a sagittal plane of best fit through the spine centerline;

determining a second plane, perpendicular to the first plane, which is a coronal plane of best fit to the spine centerline;

projecting the image of the spine onto the second plane to generate a projection of the image of the spine onto the second plane;

displaying of the determined second plane, and displaying the generated projection of the image of the spine onto the second plane; and deriving a measure of fit error of the determined spine centerline to the first plane;

wherein if the measure of fit error is below a threshold, displaying the first plane and the image of the spine, and wherein if the measure of fit error is not below the threshold, projecting the image of the spine onto the first plane to generate a projection of the image of the spine onto the first plane, and displaying the first plane and the generated projected image of the spine onto the first plane.

11. The ultrasound system of claim 8, wherein the first plane is the mid-sagittal plane.

12. The ultrasound system of claim 8, wherein if the measure of fit error is above a second threshold, the controller is adapted to provide an output indicating high spine curvature.

13. The ultrasound system of claim 8, wherein controller is further adapted to derive a measure of fit error of the spine centerline to the second plane, wherein if the measure of fit error is above a third threshold, providing an output indicating high spine curvature.

14. The ultrasound system of claim 8, wherein controller is further adapted to derive a sequence of planes perpendicular to the spine centerline.

15. The ultrasound system of claim 8, further comprising a user interface allowing a user to sweep though the sequence in order to view each vertebra in an axial view.

16. The ultrasound system of claim 8, wherein controller is further adapted to define a volume of interest around the spine and performing volume rendering.

17. The non-transitory storage medium of claim 10, wherein if the measure of fit error is above a second threshold, providing an output indicating high spine curvature.

18. The non-transitory storage medium of claim 10, further comprising deriving a measure of fit error of the spine centerline to the second plane, wherein if the measure of fit error is above a third threshold, providing an output indicating high spine curvature.

19. The non-transitory storage medium of claim 10, further comprising a user interface allowing a user to sweep though the sequence in order to view each vertebra in an axial view via a user interface.

20. The method of claim 1, further comprising defining a volume of interest around the spine and performing volume rendering.

* * * * *